US010624980B2

(12) United States Patent
Ye et al.

(10) Patent No.: US 10,624,980 B2
(45) Date of Patent: Apr. 21, 2020

(54) VEHICLE-MOUNTED AROMA DIFFUSER

(71) Applicant: Shenzhen Huiqimei Technology Co., Ltd., Shenzhen, Guangdong Province (CN)

(72) Inventors: Jianling Ye, Shenzhen (CN); Zengtong Lin, Shenzhen (CN)

( * ) Notice: Subject to any disclaimer, the term of this patent is extended or adjusted under 35 U.S.C. 154(b) by 367 days.

(21) Appl. No.: 15/644,598

(22) Filed: Jul. 7, 2017

(65) Prior Publication Data

US 2018/0200400 A1     Jul. 19, 2018

(30) Foreign Application Priority Data

Jan. 16, 2017   (CN) .......................... 2017 1 0028837
Jan. 16, 2017   (CN) ..................... 2017 2 0047041 U

(51) Int. Cl.
| | |
|---|---|
| *A61L 9/03* | (2006.01) |
| *B60H 3/00* | (2006.01) |
| *A61L 9/015* | (2006.01) |
| *A61L 9/14* | (2006.01) |
| *A61L 9/00* | (2006.01) |

(52) U.S. Cl.
CPC ................ *A61L 9/03* (2013.01); *A61L 9/015* (2013.01); *A61L 9/14* (2013.01); *B60H 3/00* (2013.01); *A61L 9/00* (2013.01); *A61L 2209/132* (2013.01); *A61L 2209/133* (2013.01)

(58) Field of Classification Search
CPC ................ A61L 9/03; A61L 9/00; B60H 3/00
USPC .... 392/386, 387, 390, 391, 393; 239/34, 44, 239/55, 59
See application file for complete search history.

(56) References Cited

U.S. PATENT DOCUMENTS

| | | | | | |
|---|---|---|---|---|---|
| 1,577,604 | A | * | 3/1926 | Bauer ....................... | A61L 9/03 422/125 |
| 4,219,531 | A | * | 8/1980 | Wisniewski .............. | A61L 9/03 261/DIG. 88 |
| 5,394,506 | A | * | 2/1995 | Stein ......................... | A61L 9/03 219/202 |
| 5,647,052 | A | * | 7/1997 | Patel .................... | A01M 1/2083 392/390 |
| 6,021,254 | A | * | 2/2000 | Hunter ....................... | A61L 9/03 261/DIG. 65 |
| 6,085,026 | A | * | 7/2000 | Hammons ................. | A61L 9/03 219/544 |
| 6,413,476 | B1 | * | 7/2002 | Barnhart ................... | A61L 9/03 422/123 |
| 6,592,828 | B2 | * | 7/2003 | Quintana Munoz ........................ | A01M 1/2077 392/390 |
| D486,213 | S | * | 2/2004 | Novak ......................... | D23/366 |

(Continued)

*Primary Examiner* — Jimmy Chou
(74) *Attorney, Agent, or Firm* — Novoclaims Patent Services LLC; Mei Lin Wong

(57) ABSTRACT

Disclosed is a vehicle-mounted aroma diffuser comprising a main unit shell, an integral vehicle charging plug support, a motor, a fan, a main unit circuit board, an atomizer and a water tank. The integral vehicle charging plug support and the main unit shell of the vehicle-mounted aroma diffuser are integrally and rotatably connected, the angle of the aroma diffuser can be adjusted according to actual requirements when the aroma diffuser is in use, the disordered wiring method of traditional split-type vehicle charger supports can be changed, the space in the vehicle is cleaner and tidier, and usage is more convenient through the integral instant-plugging design.

16 Claims, 5 Drawing Sheets

(56) References Cited

U.S. PATENT DOCUMENTS

| | | | | |
|---|---|---|---|---|
| D604,699 S * | 11/2009 | Yamamoto | | D13/108 |
| 8,197,761 B1 * | 6/2012 | Miller-Larry | | A61L 9/032 |
| | | | | 392/390 |
| 8,262,277 B2 * | 9/2012 | Hsiao | | A61L 9/03 |
| | | | | 362/643 |
| 8,364,028 B1 * | 1/2013 | Vaske | | A61L 9/03 |
| | | | | 219/385 |
| D692,548 S * | 10/2013 | Wirz | | D23/366 |
| D692,550 S * | 10/2013 | Wirz | | D23/366 |
| 8,662,480 B1 * | 3/2014 | Irvin | | B60H 3/0028 |
| | | | | 261/26 |
| 8,673,223 B1 * | 3/2014 | Finlay | | A61L 9/122 |
| | | | | 239/34 |
| 8,750,694 B1 * | 6/2014 | Porretta | | B60H 3/0028 |
| | | | | 392/395 |
| 8,765,073 B1 * | 7/2014 | Hsiao | | A61L 2/00 |
| | | | | 239/34 |
| 8,983,277 B2 * | 3/2015 | Hsiao | | A61L 9/03 |
| | | | | 392/386 |
| 9,031,392 B2 * | 5/2015 | Hsiao | | A61L 9/03 |
| | | | | 392/394 |
| 9,410,695 B2 * | 8/2016 | Hsiao | | A61L 9/03 |
| 9,500,358 B2 * | 11/2016 | Hsiao | | A61L 9/03 |
| 9,844,609 B2 * | 12/2017 | Hsiao | | A61L 9/03 |
| 10,064,969 B2 * | 9/2018 | Hsiao | | A61L 9/03 |
| 10,179,184 B2 * | 1/2019 | Belz | | A61L 9/03 |
| 10,225,885 B2 * | 3/2019 | Belongia | | H05B 3/0052 |
| 2002/0023968 A1 * | 2/2002 | Pedrotti | | A01M 1/2061 |
| | | | | 239/60 |
| 2002/0176704 A1 * | 11/2002 | Roe | | A61L 9/03 |
| | | | | 392/393 |
| 2004/0003724 A1 * | 1/2004 | Ellis | | A01M 1/205 |
| | | | | 96/115 |
| 2004/0016818 A1 * | 1/2004 | Murdell | | A01M 1/2033 |
| | | | | 239/34 |
| 2004/0022675 A1 * | 2/2004 | An | | A61L 9/02 |
| | | | | 422/29 |
| 2005/0013728 A1 * | 1/2005 | Huang | | A61L 9/03 |
| | | | | 422/4 |
| 2005/0016985 A1 * | 1/2005 | Haas | | A61L 9/03 |
| | | | | 219/438 |
| 2005/0274818 A1 * | 12/2005 | Ghazarian | | A61L 9/02 |
| | | | | 239/34 |
| 2006/0091570 A1 * | 5/2006 | Reece | | A01M 1/2066 |
| | | | | 261/19 |
| 2006/0193610 A1 * | 8/2006 | Han | | A61L 9/03 |
| | | | | 392/390 |
| 2006/0196964 A1 * | 9/2006 | Wheatley | | A61L 9/03 |
| | | | | 239/57 |
| 2007/0014549 A1 * | 1/2007 | Demarest | | A61M 11/041 |
| | | | | 392/393 |
| 2007/0047931 A1 * | 3/2007 | Niemeyer | | A61L 9/03 |
| | | | | 392/390 |
| 2007/0217771 A1 * | 9/2007 | Granger | | A01M 1/2033 |
| | | | | 392/386 |
| 2007/0284765 A1 * | 12/2007 | Wang | | A61L 9/03 |
| | | | | 261/142 |
| 2008/0013932 A1 * | 1/2008 | He | | A01M 1/2072 |
| | | | | 392/390 |
| 2008/0178518 A1 * | 7/2008 | Reece | | A01M 1/2066 |
| | | | | 43/127 |
| 2009/0200393 A1 * | 8/2009 | Avelar | | A61L 9/03 |
| | | | | 239/60 |
| 2010/0001417 A1 * | 1/2010 | D'Amico | | A61L 9/012 |
| | | | | 261/26 |
| 2010/0129157 A1 * | 5/2010 | Reddy | | A01M 17/002 |
| | | | | 405/128.7 |
| 2010/0150774 A1 * | 6/2010 | Marchetti | | A01M 1/2033 |
| | | | | 422/5 |
| 2010/0260491 A1 * | 10/2010 | Pitz | | A01M 1/2061 |
| | | | | 392/390 |
| 2010/0266266 A1 * | 10/2010 | Garcia Fabrega | | A61L 9/037 |
| | | | | 392/395 |
| 2010/0270943 A1 * | 10/2010 | Cook | | A61L 9/03 |
| | | | | 315/291 |
| 2010/0288847 A1 * | 11/2010 | Gruenbacher | | A01M 1/2033 |
| | | | | 239/34 |
| 2011/0221078 A1 * | 9/2011 | Lev | | A61L 9/03 |
| | | | | 261/81 |
| 2012/0093491 A1 * | 4/2012 | Browder | | A61L 9/015 |
| | | | | 392/390 |
| 2012/0183280 A1 * | 7/2012 | Kowalec | | A61L 9/03 |
| | | | | 392/386 |
| 2014/0014641 A1 * | 1/2014 | Propes | | A61L 9/03 |
| | | | | 219/421 |
| 2014/0112649 A1 * | 4/2014 | Irvin | | A61L 9/03 |
| | | | | 392/390 |
| 2014/0126892 A1 * | 5/2014 | Hsiao | | B60H 3/0007 |
| | | | | 392/394 |
| 2014/0126893 A1 * | 5/2014 | Hsiao | | A61L 9/03 |
| | | | | 392/403 |
| 2014/0133841 A1 * | 5/2014 | Hsiao | | A61L 9/16 |
| | | | | 392/386 |
| 2014/0334801 A1 * | 11/2014 | Browder | | A61L 9/03 |
| | | | | 392/390 |
| 2015/0109823 A1 * | 4/2015 | Hsiao | | A61L 9/03 |
| | | | | 362/643 |
| 2016/0015847 A1 * | 1/2016 | Irvin | | A61L 9/03 |
| | | | | 392/390 |
| 2016/0022855 A1 * | 1/2016 | Esses | | B60H 3/0007 |
| | | | | 392/386 |
| 2016/0022857 A1 * | 1/2016 | Esses | | A61L 9/032 |
| | | | | 392/390 |
| 2016/0045632 A1 * | 2/2016 | Moenkemoeller | | A61L 9/03 |
| | | | | 239/8 |
| 2016/0325000 A1 * | 11/2016 | Lal | | A61L 9/03 |
| 2017/0072086 A1 * | 3/2017 | Gruenbacher | | A61L 9/14 |
| 2017/0112955 A1 * | 4/2017 | Bourne | | A61L 9/125 |
| 2017/0128608 A1 * | 5/2017 | Hsiao | | A61L 9/03 |
| 2017/0165390 A1 * | 6/2017 | Gruenbacher | | A61L 9/14 |
| 2018/0228930 A1 * | 8/2018 | Davis | | A61L 9/03 |
| 2019/0022270 A1 * | 1/2019 | Yang | | A61L 9/22 |

* cited by examiner

VEHICLE-MOUNTED AROMA DIFFUSER

BACKGROUND OF THE INVENTION

Technical Field

The invention relates to the technical field of vehicle-mounted equipment, in particular to a vehicle-mounted aroma diffuser.

Description of Related Art

High-frequency vibration generated by an aroma diffuser through ultrasonic vibrating equipment decomposes water molecules and dissolved plant essential oil into nanoscale cold mist with the diameter being 0.1-5 microns, and the nanoscale cold mist is diffused into the surrounding air, so that the air is full of fragrance. Indoor air is dry after heating in winter, and consequentially, 'heating dryness' symptoms such as lip chapping, pharynx dryness, hoarseness, bitter tastes, dry cough, skin dryness and nosebleeds can happen to people. The aroma diffuser atomizes water and pure plant essential oil in many ways, so that the humidity of a room is kept high, a certain quantity of natural negative oxygen ions are generated, an aromatic therapy effect is achieved while the air is purified, adjuvant therapy and relieving of diseases such as flu, hypertension and trachitis can be achieved, and the nervous system, the cardiovascular system and the metabolism of people are protected to a certain extent.

Aromatherapy is a fashion, a culture and a spiritual sustenance method for people pursuing a high-grade life. According to the structure of an existing aroma diffuser sold on the market, due to the fact that circuit devices such as a circuit board and a fan are all arranged on a base below a water tank, the aroma diffuser cannot incline by a large gradient in the using process for preventing short circuits and burnout of the devices such as the circuit board caused by pouring-out of water in the water tank, and thereof, an aroma diffuser which can be used inside a bumping vehicle is not available yet on the market currently.

BRIEF SUMMARY OF THE INVENTION

The invention aims to provide a vehicle-mounted aroma diffuser to solve the problems mentioned in the background art.

According to the technical scheme provided by the invention for achieving the aim: a vehicle-mounted aroma diffuser comprises a main unit shell, an integral vehicle charging plug support, a motor, a fan, a main unit circuit board, an atomizer and a water tank, wherein the main unit shell comprises a main unit upper shell and a main unit lower shell which are each of a hollow structure with the upper portion and the lower portion being open, the lower end of the main unit upper shell is inserted into the main unit lower shell, a containing space is formed between the outer surface of the lower end of the main unit upper shell and the inner surface of the main unit lower shell, and the main unit circuit board is mounted inside the main unit lower shell and arranged in the containing space of the main unit lower shell;

the periphery of the motor is wrapped with a motor waterproof device, the fan is rotatably connected with the motor, and the motor is mounted inside the main unit upper shell;

an atomization piece support is mounted at the lower end of the main unit lower shell and arranged inside the water tank; the water tank is mounted at the lower end of the main unit lower shell; the integral vehicle charging plug support is rotatably connected with the main unit lower shell.

Preferably, the motor waterproof device comprises a motor case upper shell, a motor case waterproof ring, a motor case lower shell and a motor waterproof ring, wherein the motor case upper shell and the motor case lower shell are connected in a buckled mode through a locking piece, the motor case waterproof ring is arranged at the position where the motor case upper shell and the motor case lower shell are buckled, the motor is arranged inside the motor waterproof device, a through hole is formed in the central position of the motor case lower shell, a motor rotary shaft stretches out from the through hole, and the motor waterproof ring is arranged on the periphery of the through hole and located on the contact surface of the motor case lower shell and the motor.

Preferably, a key and a key circuit board are arranged inside the motor waterproof device, the key is arranged in a key through hole of the motor case upper shell and stretches out from the key through hole, the key circuit board is correspondingly arranged under the key and connected with the key in a contact mode, a motor key wiring hole is formed in the motor case lower shell, and the key circuit board is electrically connected with the main unit circuit board through wiring of the motor key wiring hole.

Preferably, the main unit upper shell is provided with an upper shell key wiring hole, the upper shell key wiring hole is correspondingly connected with the motor key wiring hole, and a motor key wiring waterproof ring is arranged between the upper shell key wiring hole and the motor key wiring hole; a main unit upper cover is arranged at an opening in the upper end of the main unit upper shell, the main unit upper cover is mounted on the main unit upper shell, continuous seams are reserved in the main unit upper cover and the edge of the opening of the main unit upper shell, a through hole is formed in the position, corresponding to the key, of the main unit upper cover, and the key stretches out from the through hole.

Preferably, the atomizer (3) comprises an atomization piece support (13) and an atomization piece (14), and the atomization piece support is mounted at the lower end of the main unit lower shell.

Preferably, the integral vehicle charging plug support comprises a main unit support, a vehicle charger mainboard, a vehicle charger shell, a vehicle charger contact chip and an expansion USB interface, wherein the main unit support is arranged at the upper end of the vehicle charger shell and fixedly connected with the vehicle charger shell, the vehicle charger mainboard is arranged inside the vehicle charger shell, the vehicle charger contact chip is arranged in a through hole in the bottom end of the vehicle charger shell and stretches out from the through hole, the vehicle charger contact chip is electrically connected with the vehicle charger mainboard, the vehicle charger mainboard is electrically connected with the main unit circuit board, and the expansion USB interface is arranged on the vehicle charger mainboard and stretches out from a through hole in the surface of the vehicle charger shell.

Preferably, the main unit support is of a U-shaped structure.

Preferably, two mounting holes are formed in opposite positions of the side face of the main unit lower shell, two mounting buckle keys are arranged on the U-shaped opening of the main unit support correspondingly, and the mounting buckle keys are mounted in the mounting holes in a buckled mode.

Preferably, corresponding limiting toothed structures are arranged on the inner walls of the mounting holes and the outer walls of the mounting buckle keys respectively.

Preferably, a mist outlet channel isolation connector is arranged at the upper end of the atomization piece support, the upper edge of the mist outlet channel isolation connector is connected with the lower edge of the main unit upper shell in a joint mode, and an atomization piece support waterproof ring is arranged at the joint of the mist outlet channel isolation connector and the main unit upper shell; a lower support bracket is arranged at the lower end of the atomization piece support, a water inlet and a mist nozzle are arranged on the upper surface of the lower support bracket, and an atomization piece is arranged at the position, corresponding to the mist nozzle, of the lower surface of the lower support bracket; an atomization piece cover is arranged under the atomization piece, and the atomization piece waterproof ring is arranged between the atomization piece cover and the lower support bracket; the mist outlet channel isolation connector is integrally connected with the lower support bracket through a connecting column; the atomization piece is electrically connected with the main unit circuit board.

Compared with the prior art, the invention has the beneficial effects that the vehicle-mounted aroma diffuser is provided with an omnibearing waterproof structure, the fan and the motor are arranged above the water tank, waterproof protection of the motor and the key circuit board is achieved through the motor waterproof device, and thus the motor and the key circuit board are prevented from being affected by water mist; the main unit circuit board is mounted in the isolation space formed by the main unit upper shell and the main unit lower shell, and thus a waterproof effect can be achieved; the wiring hole and the waterproof ring are arranged in a combined mode in the circuit wiring process, and thus the aroma diffuser can be used in the space in a vehicle through the omnibearing waterproof design; meanwhile, the integral vehicle charging plug support is integrally and rotatably connected with the main unit shell so that the angle of the aroma diffuser can be adjusted according to actual requirements when the aroma diffuser is in use, a disordered wiring way of a traditional split-type vehicle charger support can be changed, the space in the vehicle is cleaner and tidier, and using is more convenient through the integral instant-plugging design; the opening in the upper end of the main unit upper shell serves as an air inlet/outlet, both air and mist enter and come out through the opening when the fan works, the mode that an air inlet, an air outlet and a mist outlet need to be arranged for the traditional aroma diffuser is changed, multiple purposes are achieved through the opening, and the structure of the product is optimized.

In FIGs: 1—main unit shell, 11—main unit upper shell, 111—upper shell key wiring hole, 112—air inlet/outlet, 12—main unit lower shell, 121—mounting hole, 13—atomization piece support, 131—mist outlet channel isolation connector, 132—connecting column, 133—mist nozzle, 134—water inlet, 135—lower support bracket, 136—atomization piece support waterproof ring, 14—atomization piece, 15—atomization piece waterproof ring, 16—atomization piece cover, 2—motor waterproof device, 21—motor case upper shell, 22—motor case waterproof ring, 23—motor case lower shell, 231—motor key wiring hole, 24—motor key wiring waterproof ring, 25—motor waterproof ring, 3—atomizer, 4—integral vehicle charging plug support, 41—main unit support, 411—mounting buckle key, 412—limiting toothed structure, 42—vehicle charger mainboard, 43—vehicle charger shell, 44—vehicle charger contact chip, 45—expansion USB interface, 5—main unit upper cover, 6—key, 7—key circuit board, 8—motor, 9—fan, 10—main unit circuit board, 17—water tank, 171—main unit lower shell waterproof ring.

DETAILED DESCRIPTION OF THE INVENTION

A clear and complete description of the technical scheme in the embodiment of the invention is given with the drawings in the embodiment of the invention as follows, and obviously, the described embodiment is only part of embodiments of the invention and not all embodiments of the invention. Based on the embodiment of the invention, all other embodiments obtained by ordinary technicians in the field without any creative work are within the protection scope of the invention.

Figure 1:
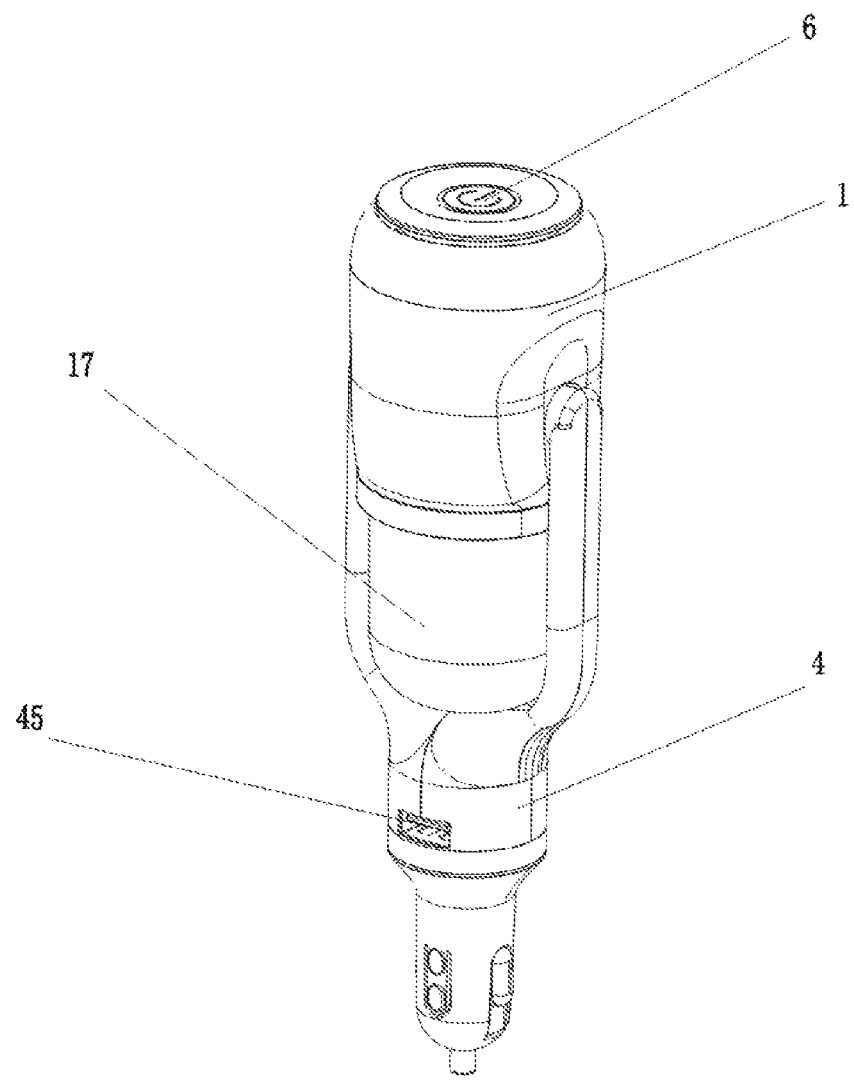
FIG. 1 is an overall structure schematic diagram of the invention.
Figure 2A:
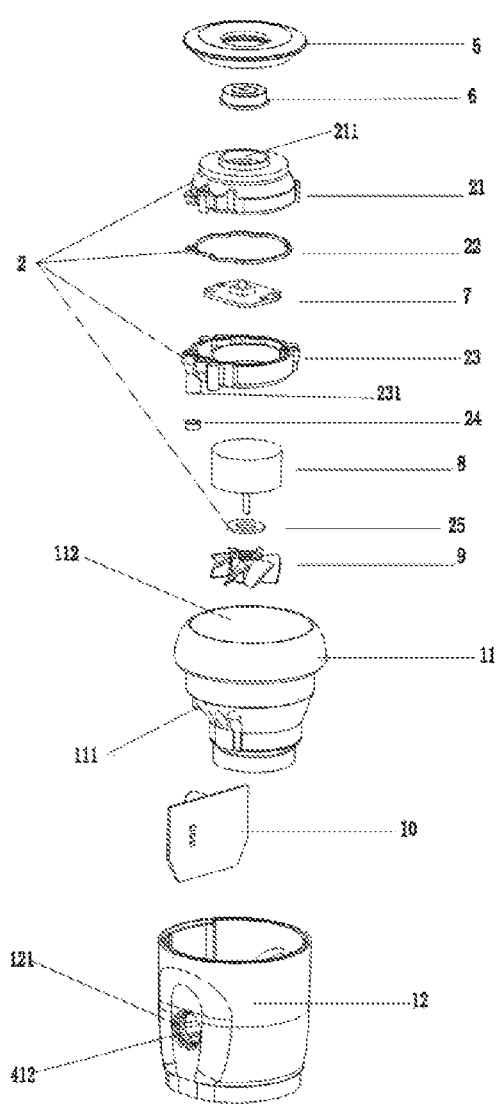
FIGS. 2A and 2B are an overall structure explosive view of the invention.
Figure 2B:
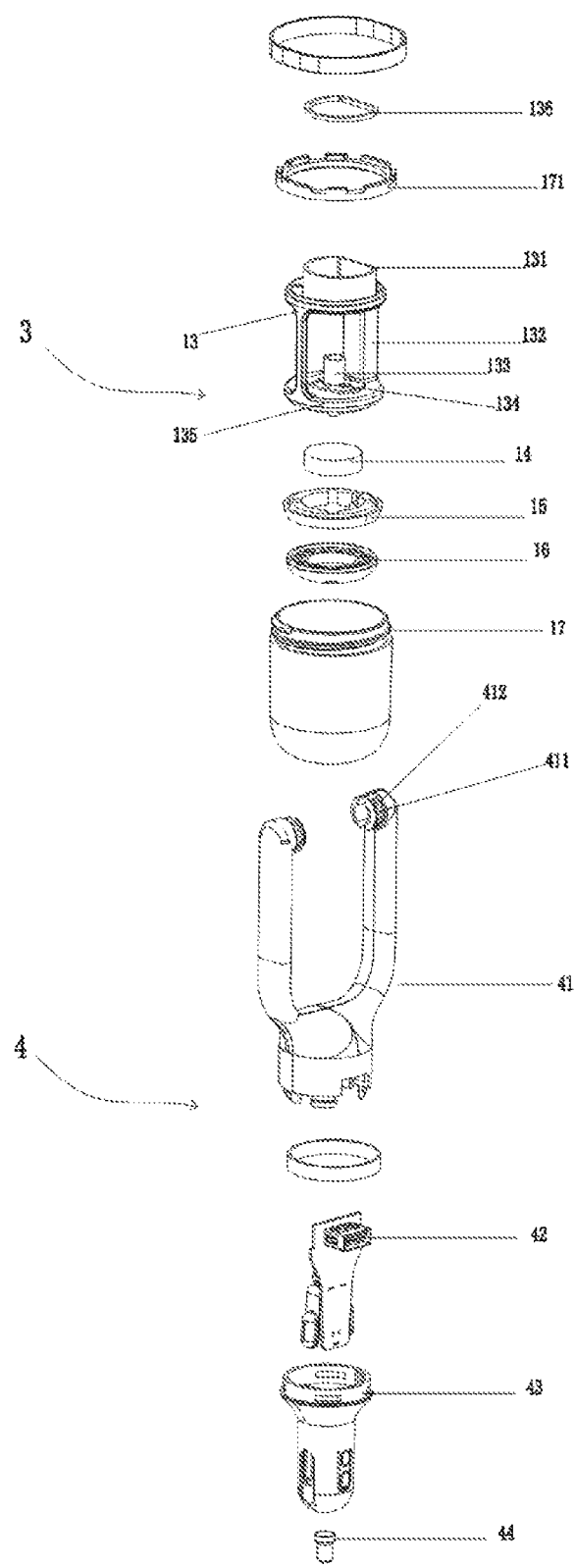
Figure 3:
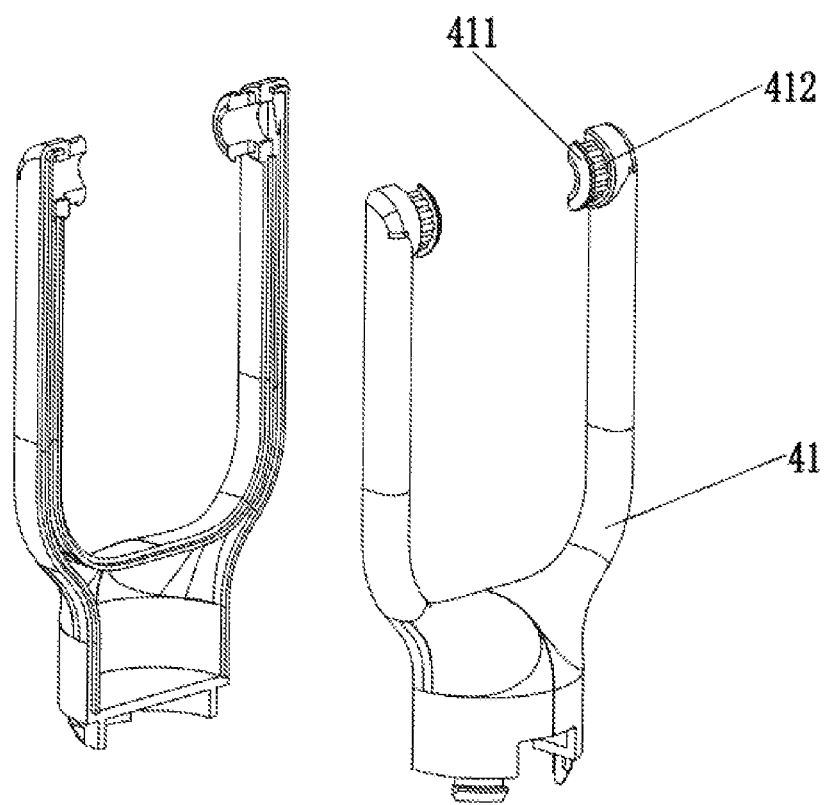
FIG. 3 is a structure schematic diagram of an integral vehicle charging plug support of the invention.
Figure 4:
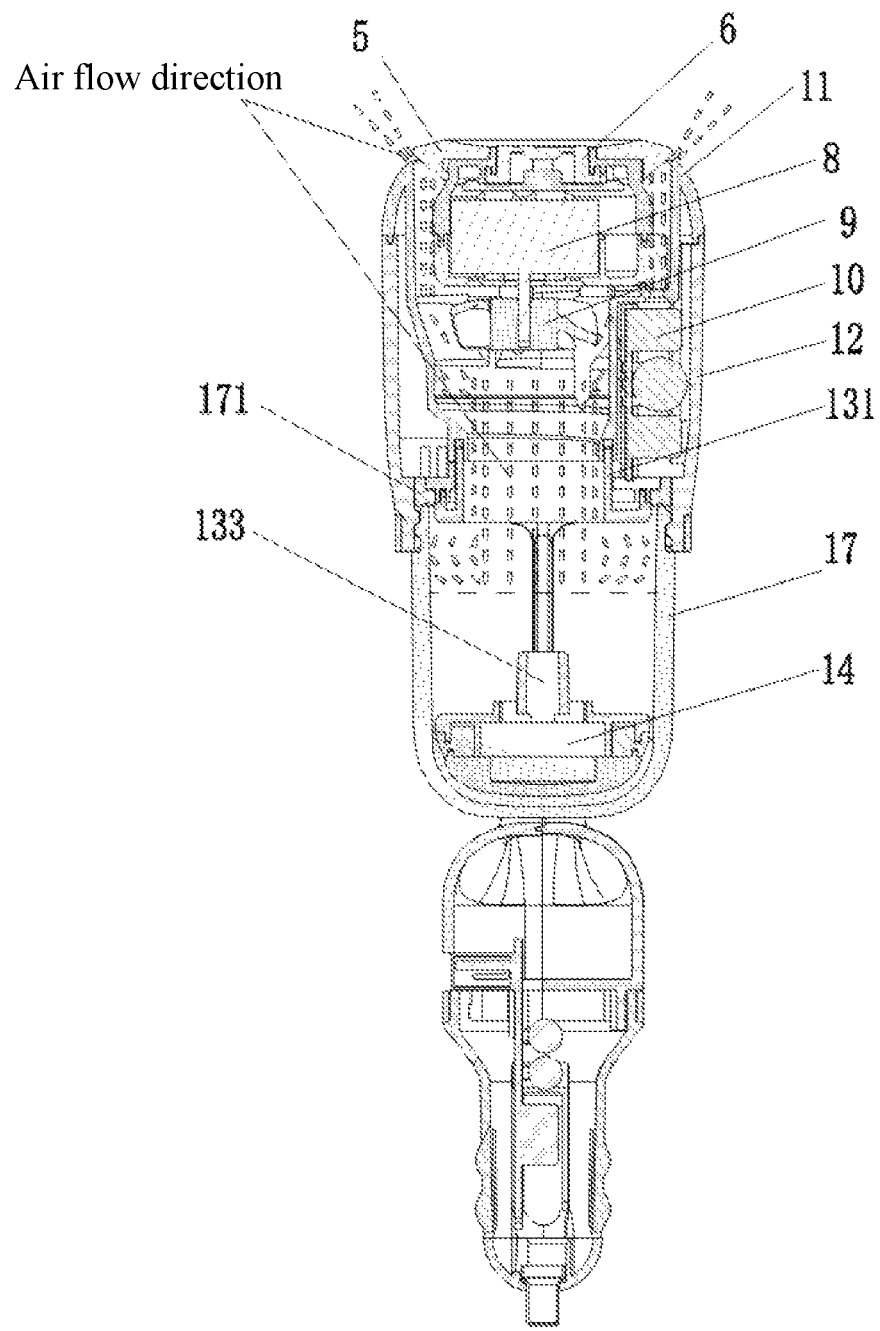
FIG. 4 is a sectional structure schematic diagram of the invention.

Please see FIGS. 1-4, according to the technical scheme provided by the invention: a vehicle-mounted aroma diffuser comprises a main unit shell 1, an integral vehicle charging plug support 4, a motor 8, a fan 9, a main unit circuit board 10, an atomizer 3 and a water tank 17, wherein the main unit shell 1 comprises a main unit upper shell 11 and a main unit lower shell 12 which are each of a hollow structure with the upper portion and the lower portion being open, the lower end of the main unit upper shell 11 is inserted into the main unit lower shell 12, a containing space is formed between the outer surface of the lower end of the main unit upper shell 11 and the inner surface of the main unit lower shell 12, the main unit circuit board 10 is mounted in the main unit lower shell 12 and located in the containing space of the main unit lower shell 12, and waterproof isolation of the main unit circuit board 10 relative to the outside space is achieved;

the water tank 17 is mounted at the lower end of the main unit lower shell 12, and a main unit lower shell waterproof ring 171 is arranged at the junction of the water tank 17 and the main unit lower shell 12; an atomization piece support 4 is mounted at the lower end of the main unit lower shell 12 and arranged inside the water tank 17, a mist outlet channel isolation connector 131 is arranged at the upper end of the atomization piece support 13, the upper edge of the mist outlet channel isolation connector 131 is connected with the lower edge of the main unit upper shell 11 in a joint mode, and an atomization piece support waterproof ring 136 is arranged at the joint of the mist outlet channel isolation connector 131 and the main unit upper shell 11; in this way, a communicating space is formed by the water tank 17, the mist outlet channel isolation connector 131 and an inner cavity of the main unit upper shell 11 and serves as a water mist generation area, water mist generated in the space cannot permeate into the containing space where the main unit circuit board 10 is located, and the main unit circuit board 10 can be effectively protected against damage caused by influences of the water mist;

a lower support bracket 135 is arranged at the lower end of the atomization piece support 13, a water inlet 134 and a mist nozzle 133 are arranged on the upper surface of the lower support bracket 135, and an atomization piece 14 is arranged at the position, corresponding to the mist nozzle 133, of the lower surface of the lower support bracket 135; an atomization piece cover 16 is arranged under the atomization piece 14, and an atomization piece waterproof ring 15 is arranged between the atomization piece cover 16 and the lower support bracket 135; it is ensured that water in the water tank 17 cannot flow into the space below the atomization piece 14, and thus the atomization piece 14 is protected; the mist outlet channel isolation connector 131 is integrally connected with the lower support bracket 135 through a connecting column 132; a through hole used for wiring of the atomization piece 14 is formed inside the connecting column 132, and the atomization piece 14 is electrically connected with the main unit circuit board 10 through the through hole.

Two mounting holes 121 are formed in opposite positions of the side face of the main unit lower shell 12, two mounting buckle keys 411 are arranged on the U-shaped opening of the main unit support 41 correspondingly, and the mounting buckle keys 411 are mounted in the mounting holes 121 in a buckled mode; integral and rotatable connection of the integral vehicle charging plug support 4 and the main unit lower shell 12 is achieved; corresponding limiting toothed structures 412 are arranged on the inner walls of the mounting holes 121 and the outer walls of the mounting buckle keys 411 respectively, and positioning and limiting effects can be achieved when the main unit shell 1 is rotated through the limiting toothed structures 412;

the integral vehicle charging plug support 4 comprises a main unit support 41, a vehicle charger mainboard 42, a vehicle charger shell 43, a vehicle charger contact chip 44 and an expansion USB interface 45, wherein the main unit support 41 is arranged at the upper end of the vehicle charger shell 43 and fixedly connected with the vehicle charger shell 43, the vehicle charger mainboard 42 is arranged inside the vehicle charger shell 43, the vehicle charger contact chip 44 is arranged in a through hole in the bottom end of the vehicle charger shell 43 and stretches out from the through hole, the vehicle charger contact chip 44 is electrically connected with the vehicle charger mainboard 42, the vehicle charger mainboard 42 is electrically connected with the main unit circuit board 10, and the expansion USB interface 45 is arranged on the vehicle charger mainboard 42 and stretches out from a through hole in the surface of the vehicle charger shell 43; the aroma diffuser can be electrically connected with a lighting jack inside a vehicle through a vehicle charging plug device at the lower end of the integral vehicle charging plug support 4, and a vehicle-mounted instant-plugging power supply function of the aroma diffuser is achieved accordingly.

The main unit support 41 in the embodiment is of a U-shaped structure, can also be in other shapes and can adopt other structure design which can achieve the same functions.

The motor 8 is mounted at the upper end of the interior of the main unit upper shell 11, the fan 9 is rotatably connected with the motor 8, the periphery of the motor 8 is wrapped with a motor waterproof device 2, the motor waterproof device 2 comprises a motor case upper shell 21, a motor case waterproof ring 22, a motor case lower shell 23 and a motor waterproof ring 25, the motor case upper shell 21 and the motor case lower shell 23 are connected in a buckled mode through a locking piece, the motor case waterproof ring 22 is arranged at the position where the motor case upper shell 21 and the motor case lower shell 23 are buckled, the motor 8 is arranged inside the motor waterproof device 2, a through hole is formed in the central position of the motor case lower shell 23, a motor rotary shaft stretches out from the through hole, and the motor waterproof ring 25 is arranged on the periphery of the through hole and located on the contact surface of the motor case lower shell 23 and the motor 8; a key 6 and a key circuit board 7 are arranged inside the motor waterproof device 2, the key 6 is arranged in a key through hole of the motor case upper shell 21 and stretches out from the key through hole, the key circuit board 7 is correspondingly arranged under the key 6 and connected with the key 6 in a contact mode, a motor key wiring hole 231 is formed in the motor case lower shell 23, and the key circuit board 7 is electrically connected with the main unit circuit board 10 through wiring of the motor key wiring hole 231; an upper shell key wiring hole 111 is correspondingly formed in the main unit upper shell 11 and correspondingly connected with the motor key wiring hole 231, and a motor key wiring waterproof ring 24 is arranged between the upper shell key wiring hole 111 and the motor key wiring hole 231; waterproof protection of the motor 8 is achieved through the motor waterproof device 2, and thus short-circuit damage of the motor and the key circuit board 7 caused by water mist entering the motor waterproof device 2 is avoided.

The opening in the upper end of the main unit upper shell 11 serves as an air inlet/outlet 112, air enters through the air inlet/outlet 112 when the fan 9 works, part of air under pressure inside the main unit upper shell 11 can be blown out from the air inlet/outlet 112 by carrying with mist when the air pressure in the main unit upper shell 11 is increased, and the air is diffused into the peripheral space of the aroma diffuser accordingly; a main unit upper cover 5 is arranged at the air inlet/outlet 112, the main unit upper cover 5 is mounted on the main unit upper shell 11, continuous seams are reserved in the main unit upper cover 5 and the edge of the opening of the main unit upper shell 11, the main unit upper cover is used for decorating and beautifying, and the continuous seams are used for air intake and exhaust; a through hole is formed in the position, corresponding to the key 6, of the main unit upper cover 5, and the key 6 stretches out from the through hole.

Specific using method of the aroma diffuser: when the aroma diffuser of the invention is used, a proper amount of water and a proper amount of essential oil are added into the water tank 17, the atomization support 13 is arranged in the water tank 17 in a sleeved mode, then the water tank 17 is screwed and mounted at the lower end of the main unit shell 1, a vehicle charger body at the lower end of the integral vehicle charging plug support 4 is inserted into a lighting jack in the vehicle, the main unit shell 1 and the integral vehicle charging plug support 4 are rotated properly according to the actual condition to change the relative positions, pressure is applied to press the key 6, and the circuit of the aroma diffuser is closed and the aroma diffuser starts to work at the moment; the water and essential oil mixed in the water tank 17 are delivered to the atomization piece 14 through the water inlet 134, water molecules and the dissolved plant essential oil are decomposed into nanoscale cold mist through the atomization piece 14, and the nanoscale cold mist is then sprayed out through the mist nozzle 133; water mist enters the communicating space (namely the water mist generation area) formed by the water tank 17, the mist outlet channel isolation connector 131 and the inner cavity of the main unit upper shell 11 after penetrating out of the water surface in the water tank 17, blades of the fan 9 are driven by the motor 8 to blow air downwards at the moment, air flow is forcibly blown out from the air inlet/outlet 112 backwards when reaching the water surface in the water tank 17 under the pressure application effect of supplied air, the air flow carrying with the water mist having the aromatherapy effect is blown out at the moment, the water mist is diffused to the outside of the aroma diffuser accordingly, and the aromatherapy function is achieved.

The foregoing description is only the preferred specific embodiment of the invention, however, the protection scope of the invention is not limited by the foregoing description, and equivalent substitutes or changes made by any technicians familiar with the technical field in the technical scope disclosed by the invention according to the technical scheme and other inventive concepts of the invention should be included in the protection scope of the invention.

What is claimed is:

1. A vehicle-mounted aroma diffuser, comprising a main unit shell (1), an integral vehicle charging plug support (4), a motor (8), a fan (9) rotatably connected to the motor (8), a main unit circuit board (10) electrically connected to the integral vehicle charging plug support (4) and the motor (8) respectively, an atomizer (3) electrically connected to the main unit circuit board (10) and a water tank (17); characterized in that the main unit shell (1) comprises a main unit upper shell (11) and a main unit lower shell (12) which are each of a hollow structure with an upper portion and a lower portion being open, a lower end of the main unit upper shell (11) is inserted into the main unit lower shell (12), a containing space is formed between an outer surface of the lower end of the main unit upper shell (11) and an inner surface of the main unit lower shell (12), and the main unit circuit board (10) is mounted in the main unit lower shell (12) and arranged in the containing space of the main unit lower shell (12);

a periphery of the motor (8) is wrapped with a motor waterproof device (2), the fan (9) is rotatably connected with the motor (8), and the motor (8) is mounted inside the main unit upper shell (11);

the atomizer (3) is mounted at a lower end of the main unit lower shell (12) and arranged inside the water tank (17); the water tank (17) is mounted at the lower end of the main unit lower shell (12); the integral vehicle charging plug support (4) is rotatably connected with the main unit lower shell (12).

2. The vehicle-mounted aroma diffuser according to claim 1, characterized in that the motor waterproof device (2) comprises a motor case upper shell (21), a motor case waterproof ring (22), a motor case lower shell (23) and a motor waterproof ring (25), wherein the motor case upper shell (21) and the motor case lower shell (23) are connected in a buckled mode through a locking piece, the motor case waterproof ring (22) is arranged at a position where the motor case upper shell (21) and the motor case lower shell (23) are buckled, the motor (8) is arranged inside the motor waterproof device (2), a through hole is formed in a central position of the motor case lower shell (23), a motor rotary shaft stretches out from the through hole, and the motor waterproof ring (25) is arranged on a periphery of the through hole and located on a surface of the motor case lower shell (23) and the motor (8).

3. The vehicle-mounted aroma diffuser according to claim 1, characterized in that a key (6) and a key circuit board (7) are arranged inside the motor waterproof device (2), the key (6) is arranged in a key through hole of the motor case upper shell (21) and stretches out from the key through hole, the key circuit board (7) is correspondingly arranged under the key (6) and connected with the key (6) in a contact mode, a motor key wiring hole (231) is formed in the motor case lower shell (23), and the key circuit board (7) is electrically connected with the main unit circuit board (10) through wiring of the motor key wiring hole (231).

4. The vehicle-mounted aroma diffuser according to claim 1, characterized in that the main unit upper shell (11) is provided with an upper shell key wiring hole (111), the upper shell key wiring hole (111) is correspondingly connected with a motor key wiring hole (231), and a motor key wiring waterproof ring (24) is arranged between an upper shell key wiring hole (111) and the motor key wiring hole (231); a main unit upper cover (5) is arranged at an opening in the upper end of the main unit upper shell (11), the main unit upper cover (5) is mounted on the main unit upper shell (11), continuous seams are reserved in the main unit upper cover (5) and the edge of the opening of the main unit upper shell (11), a through hole is formed in a position, corresponding to the key (6), of the main unit upper cover (5), and the key (6) stretches out from the through hole.

5. The vehicle-mounted aroma diffuser according to claim 1, characterized in that the atomizer (3) comprises an atomization piece support (13) and an atomization piece (14), and the atomization piece support is mounted at the lower end of the main unit lower shell.

6. The vehicle-mounted aroma diffuser according to claim 1, characterized in that the integral vehicle charging plug support (4) comprises a main unit support (41), a vehicle charger mainboard (42), a vehicle charger shell (43), a vehicle charger contact chip (44) and an expansion USB interface (45), wherein the main unit support (41) is arranged at an upper end of the vehicle charger shell (43) and fixedly connected with the vehicle charger shell (43), the vehicle charger mainboard (42) is arranged inside the vehicle charger shell (43), the vehicle charger contact chip (44) is arranged in a through hole in the bottom end of the vehicle charger shell (43) and stretches out from the through hole, the vehicle charger contact chip (44) is electrically connected with the vehicle charger mainboard (42), the vehicle charger mainboard (42) is electrically connected with the main unit circuit board (10), and the expansion USB interface (45) is arranged on the vehicle charger mainboard (42) and stretches out from a through hole in a surface of the vehicle charger shell (43).

7. The vehicle-mounted aroma diffuser according to claim 6, characterized in that the main unit support (41) is U-shaped structure.

8. The vehicle-mounted aroma diffuser according to claim 1, characterized in that two mounting holes (121) are formed in opposite positions of the side face of the main unit lower shell (12), two mounting buckle keys (411) are arranged on the U-shaped opening of the main unit support (41) correspondingly, and the mounting buckle keys (411) are mounted in the two mounting holes (121) in a buckled mode.

9. The vehicle-mounted aroma diffuser according to claim 8, characterized in that corresponding limiting toothed structures (412) are arranged on inner walls of the mounting holes (121) and outer walls of the two mounting buckle keys (411) respectively.

10. The vehicle-mounted aroma diffuser according to claim 1, characterized in that a mist outlet channel isolation connector (131) is arranged at an upper end of the atomization piece support (13), an upper edge of the mist outlet channel isolation connector (131) is connected with an lower edge of the main unit upper shell (11) in a joint mode, and an atomization piece support waterproof ring (136) is arranged at a joint of the mist outlet channel isolation connector (131) and the main unit upper shell (11); a lower support bracket (135) is arranged at a lower end of the atomization piece support (13), a water inlet (134) and a mist nozzle (133) are arranged on an upper surface of the lower support bracket (135), and an atomization piece (14) is arranged at a position, corresponding to the mist nozzle (133), of a lower surface of the lower support bracket (135); an atomization piece cover (16) is arranged under the atomization piece (14), and an atomization piece waterproof ring (15) is arranged between the atomization piece cover (16) and the lower support bracket (135); the mist outlet channel isolation connector (131) is integrally connected with the lower support bracket (135) through a connecting column (132); the atomization piece (14) is electrically connected with the main unit circuit board (10).

11. The vehicle-mounted aroma diffuser according to claim 2, characterized in that a key (6) and a key circuit board (7) are arranged inside the motor waterproof device (2), the key (6) is arranged in a key through hole of the motor case upper shell (21) and stretches out from the key through hole, the key circuit board (7) is correspondingly arranged under the key (6) and connected with the key (6) in a contact mode, a motor key wiring hole (231) is formed in the motor case lower shell (23), and the key circuit board (7) is electrically connected with the main unit circuit board (10) through wiring of the motor key wiring hole (231).

12. The vehicle-mounted aroma diffuser according to claim 3, characterized in that the main unit upper shell (11) is provided with an upper shell key wiring hole (111), the upper shell key wiring hole (111) is correspondingly connected with the motor key wiring hole (231), and a motor key wiring waterproof ring (24) is arranged between the upper shell key wiring hole (111) and the motor key wiring hole (231); a main unit upper cover (5) is arranged at an opening in the upper end of the main unit upper shell (11), the main unit upper cover (5) is mounted on the main unit upper shell (11), continuous seams are reserved in the main unit upper cover (5) and the edge of the opening of the main unit upper shell (11), a through hole is formed in the position, corresponding to the key (6), of the main unit upper cover (5), and the key (6) stretches out from the through hole.

13. The vehicle-mounted aroma diffuser according to claim 6, characterized in that two mounting holes (121) are formed in opposite positions of the side face of the main unit lower shell (12), two mounting buckle keys (411) are arranged on the U-shaped opening of the main unit support (41) correspondingly, and the mounting buckle keys (411) are mounted in the two mounting holes (121) in a buckled mode.

14. The vehicle-mounted aroma diffuser according to claim 13, characterized in that corresponding limiting toothed structures (412) are arranged on inner walls of the two mounting holes (121) and outer walls of the two mounting buckle keys (411) respectively.

15. The vehicle-mounted aroma diffuser according to claim 7, characterized in that two mounting holes (121) are formed in opposite positions of the side face of the main unit lower shell (12), two mounting buckle keys (411) are arranged on the U-shaped opening of the main unit support (41) correspondingly, and the two mounting buckle keys (411) are mounted in the two mounting holes (121) in a buckled mode.

16. The vehicle-mounted aroma diffuser according to claim 15, characterized in that corresponding limiting toothed structures (412) are arranged on inner walls of the two mounting holes (121) and outer walls of the two mounting buckle keys (411) respectively.

* * * * *